(12) United States Patent
Hanbauer et al.

(10) Patent No.: US 9,982,940 B2
(45) Date of Patent: May 29, 2018

(54) PROCESS FOR DRYING POLYMERIC MATERIALS

(71) Applicant: DPX Fine Chemicals Austria GmbH & Co KG, Linz (AT)

(72) Inventors: Martin Helmut Friedrich Hanbauer, Echt (NL); Herwig Landschützer, Echt (NL)

(73) Assignee: Patheon Austria GmbH & Co KG, Linz (AT)

( * ) Notice: Subject to any disclaimer, the term of this patent is extended or adjusted under 35 U.S.C. 154(b) by 0 days. days.

(21) Appl. No.: 14/420,165

(22) PCT Filed: Aug. 9, 2013

(86) PCT No.: PCT/EP2013/066713
§ 371 (c)(1),
(2) Date: Feb. 6, 2015

(87) PCT Pub. No.: WO2014/023826
PCT Pub. Date: Feb. 13, 2014

(65) Prior Publication Data
US 2015/0198367 A1  Jul. 16, 2015

(30) Foreign Application Priority Data

Aug. 9, 2012 (EP) .................... 12179927

(51) Int. Cl.
| | | |
|---|---|---|
| *F26B 3/00* | (2006.01) | |
| *A61K 31/785* | (2006.01) | |
| *A61K 31/78* | (2006.01) | |
| *F26B 1/00* | (2006.01) | |
| *C08G 73/02* | (2006.01) | |
| *F26B 7/00* | (2006.01) | |
| *F26B 3/06* | (2006.01) | |
| *F26B 5/00* | (2006.01) | |
| *F26B 3/08* | (2006.01) | |
| *C08F 6/00* | (2006.01) | |
| *C08J 3/00* | (2006.01) | |
| *F26B 21/14* | (2006.01) | |
| *C08F 220/06* | (2006.01) | |

(52) U.S. Cl.
CPC ............ *F26B 3/00* (2013.01); *A61K 31/78* (2013.01); *A61K 31/785* (2013.01); *C08F 6/008* (2013.01); *C08F 220/06* (2013.01); *C08G 73/02* (2013.01); *C08J 3/00* (2013.01); *F26B 1/00* (2013.01); *F26B 3/06* (2013.01); *F26B 3/08* (2013.01); *F26B 5/005* (2013.01); *F26B 7/00* (2013.01); *C08J 2333/02* (2013.01); *C08J 2379/02* (2013.01); *F26B 21/14* (2013.01); *F26B 2200/08* (2013.01)

(58) Field of Classification Search
CPC ........................................................ F26B 3/00
See application file for complete search history.

(56) References Cited

U.S. PATENT DOCUMENTS

| | | |
|---|---|---|
| 3,056,728 A | 1/1959 | Ohtaki |
| 4,132,006 A | 1/1979 | Scholz et al. |
| 4,241,514 A | 12/1980 | Scholz et al. |
| 4,319,409 A | 3/1982 | Scholz et al. |

(Continued)

FOREIGN PATENT DOCUMENTS

| | | |
|---|---|---|
| CN | 102202670 A | 9/2011 |
| CN | 104603182 A | 5/2015 |

(Continued)

OTHER PUBLICATIONS

Office Action for CN201380042356.5, dated Dec. 1, 2015, (9 pages).
Extended European Search Report for EP12179927.4, dated May 28, 2013, (12 pages).
Partial European Search Report for EP12179927.4, dated Jan. 30, 2013 (7 pages).
Notice of Preliminary Rejection for KR20157002179, dated Dec. 3, 2015 (11 pages).
IPRP for PCT/EP2013/066713, dated Feb. 19, 2015 (6 pages).
International Search Report and Written Opinion for PCT/EP2013/066713, dated Oct. 31, 2013 (9 pages).

(Continued)

*Primary Examiner* — Nicole M Buie-Hatcher
(74) *Attorney, Agent, or Firm* — Pierce Atwood LLP; Raymond G. Arner

(57) ABSTRACT

The invention relates to a process for drying a moist polymeric material to obtain a dried polymeric material, comprising the steps of: mixing the moist polymeric material with an aqueous solution of a carbohydrate to afford a mixture of the moist polymeric material with the carbohydrate; and heating and/or filtering the mixture of the moist polymeric material with the carbohydrate to remove an amount of volatiles to obtain a predried polymeric material having a volatiles content $VC_{pre-dried}$ (pre-drying step); fluidizing the pre-dried material in a fluidized bed in order to further remove an amount of volatiles to obtain the dried polymeric material having a volatiles content $VC_{dried}$ (fluidized bed drying step); and withdrawing and collecting the dried polymeric material from the fluidized bed; wherein $VC_{pre-dried}$ is higher than $VC_{dried}$ and the moist polymeric material comprises at least a polymeric material, said polymeric material comprises fluorine permanently bonded to said polymeric material. The invention further relates to a dried polymeric material obtainable by the process of the invention. Furthermore, the invention relates to various uses of the process of the invention as well as to various uses of the dried polymeric materials.

23 Claims, No Drawings

(56) References Cited

U.S. PATENT DOCUMENTS

| | | | |
|---|---|---|---|
| 4,426,507 A | 1/1984 | Kiselnikov et al. | |
| 4,730,035 A | 3/1988 | Mark et al. | |
| 5,052,123 A | 10/1991 | Tischendorf et al. | |
| 6,187,902 B1 | 2/2001 | Yanase et al. | |
| 8,791,230 B2 * | 7/2014 | Matsumoto | C08J 3/12 528/480 |
| 2004/0138542 A1 | 7/2004 | Khuri et al. | |
| 2007/0149697 A1 | 6/2007 | Klein et al. | |
| 2008/0127507 A1 * | 6/2008 | Bindelle | C08F 6/20 34/343 |
| 2010/0104527 A1 | 4/2010 | Mansky et al. | |
| 2010/0111891 A1 | 5/2010 | Albrecht et al. | |
| 2010/0111892 A1 * | 5/2010 | Chang | C08F 220/22 424/78.1 |
| 2011/0236340 A1 | 9/2011 | Mansky et al. | |
| 2012/0028016 A1 | 2/2012 | Zuercher et al. | |
| 2013/0107260 A1 | 5/2013 | Nozawa | |
| 2015/0198367 A1 | 7/2015 | Hanbauer et al. | |

FOREIGN PATENT DOCUMENTS

| | | |
|---|---|---|
| DE | 2632054 A1 | 1/1978 |
| DE | 251754 A1 | 11/1987 |
| EP | 0003120 A2 | 7/1979 |
| EP | 0260050 A1 | 3/1988 |
| EP | 0407876 A2 | 1/1991 |
| EP | 0926162 A1 | 6/1999 |
| JP | 2001-500838 A | 1/1999 |
| JP | 2011-240914 A | 9/1999 |
| JP | 2012-500806T A | 1/2012 |
| JP | 2015531016 A | 10/2015 |
| KR | 950006121 B1 | 6/1995 |
| KR | 1020010006213 A | 1/2001 |
| KR | 1020110063647 | 6/2011 |
| WO | 88/01625 A1 | 3/1988 |
| WO | 98/45032 | 10/1998 |
| WO | 2011/119422 A1 | 9/2001 |
| WO | 2004058480 A1 | 7/2004 |
| WO | 2005/097081 A1 | 10/2005 |
| WO | 2010/022381 A1 | 2/2010 |
| WO | 2010/022382 A2 | 2/2010 |
| WO | 2010/022383 A2 | 2/2010 |
| WO | 2014023826 A1 | 2/2014 |

OTHER PUBLICATIONS

First Examiners Report, CA 2879493, dated (3 pages).
Final Rejection, KR 20157002179, dated Jun. 28, 2016 7 pages.
Canadian Office Action dated Nov. 14, 2016 from corresponding Canadian Patent Application No. 2,879,493 (3 pages).
Canadian Office Action dated Aug. 8, 2017 from corresponding Canadian Patent Application No. 2,879,493 (3 pages).
European Communication pursuant to Article 94(3) dated Mar. 7, 2016 from corresponding European Patent Application No. 13750678.8 (3 pages).
European Communication Pursuant to Article 94(3) dated Oct. 26, 2016 from corresponding European Patent Application No. 13750678.8 (4 pages).
Japanese Office Action dated Mar. 8, 2016 from corresponding Japanese Patent Application No. P2015-525900 (12 pages).
Japanese Office Action dated Nov. 8, 2016 from corresponding Japanese Patent Application No. P2015-525900 (6 pages).

* cited by examiner

PROCESS FOR DRYING POLYMERIC MATERIALS

RELATED APPLICATIONS

This application is a U.S. National Stage of International Application No. PCT/EP2013/066713, filed on Aug. 9, 2013, which claims priority to European Patent Application No. 12179927.4, filed Aug. 9, 2012, and U.S. Provisional Patent Application No. 61/681,295, filed Aug. 9, 2012, the entire contents of which are incorporated herein by reference.

The present invention relates to a process for drying a moist polymeric material to obtain a dried polymeric material. The invention further relates to a dried polymeric material obtainable by the process of the invention. Furthermore, the invention relates to various uses of the process of the invention as well as to various uses of the dried polymeric materials.

The uses of polymeric materials in the modern world are multiple. Nowadays polymeric materials find applications in a variety of industries for example automotive, marine, aerospace, medical, defense, sports/recreational, architectural, bottling, household and machinery. For this reason, demand for polymeric materials is continuously growing simultaneously with stricter requirements imposed on the quality of said polymeric materials. This provides an impetus for the elaboration of processes that aim to provide higher throughput combined with enhanced purity of polymeric materials thus produced. Especially, in case of polymeric materials that are intended to be used as active pharmaceutical ingredients (API) enhanced and consistent purity is not only desirable but in certain cases required by relevant regulations. Polymeric materials may be produced in a variety of ways and polymerization techniques in the absence or presence of solvents, the latter being typically organic solvents or water. In case a polymeric material is prepared in the presence of water e.g. suspension or emulsion polymerization, or during its preparation water is used e.g. polymer is suspended in water, some amount of water needs to be driven off before the polymeric material is suitable for its intended use. The reason for that is that the amount of water present in a polymeric material may significantly affect the performance of the polymeric material; thus, it is generally desired to remove at least some of the water contained in a polymeric material. For example, polymeric materials that are intended to be used as API, they cannot always be used in the form they are initially produced, said form may be a suspension or an emulsion of the polymeric material; thus, efficient drying of said polymeric materials driving off unwanted amounts of volatiles e.g. water, is a very important step in the production of such polymeric materials since it impacts its performance and ability to be stored for long time periods.

Certain polymeric materials with fluorine bonding show limited stability above, below or between certain water content, and reliable and fast drying processes are needed to ensure long term stability. This is especially the case for APIs where quality and purity is essential.

Moreover, in the case of polymeric materials that are prepared in the presence of water e.g. suspension or emulsion polymerization, or during their preparation water is used e.g. polymer is diluted in water, once known drying processes are applied, these lead to undesired agglomeration of the polymeric material. Agglomeration is unwanted because not only affects the performance of a polymeric material but in many occasions and applications compromises the performance of the polymeric material that either increase further the cost for the preparation the polymeric material since additional and rather expensive process steps are necessary to break down those agglomerates in particles of the desired size or it is not at all possible to break down said agglomerates due to the nature of the polymeric material itself or because the additional steps required to break down said agglomerates renders is not cost effective; thus rendering certain polymeric materials commercially unattractive or unsuitable for certain applications, both of which resulting in limiting the applications of a polymeric material.

Therefore, there is a desire for at least processes that allow efficient drying of polymeric materials and at the same time said processes can provide dried polymeric materials of high purity without undesired agglomeration and prolonged storage stability. It is furthermore desirable, said drying process to be less energy demanding.

It is therefore the object of the invention to provide a process that provides for an efficient drying of polymeric materials containing permanently bonded fluorine and reduces or even eliminates agglomeration of the polymeric material during drying preferably combined with high purity of the dried polymeric material and/or prolonged storage stability, preferably also combined with lower energy demands.

The object of the invention is achieved by a process for drying a moist polymeric material to obtain a dried polymeric material, comprising the steps of:

mixing the moist polymeric material with an aqueous solution of a carbohydrate to afford a mixture of the moist polymeric material with the carbohydrate; and heating and/or filtering the mixture of moist polymeric material with the carbohydrate to remove an amount of volatiles and carbohydrate to obtain a pre-dried polymeric material having a volatiles content $VC_{pre\text{-}dried}$ (pre-drying step);

fluidizing the pre-dried material in a fluidized bed in order to further remove an amount of volatiles to obtain the dried polymeric material having a volatiles content $VC_{dried}$ (fluidized bed drying step); and withdrawing and collecting the dried polymeric material from the fluidized bed; wherein $VC_{pre\text{-}dried}$ is higher than $VC_{dried}$ and the moist polymeric material comprises at least a polymeric material, said polymeric material comprises fluorine permanently bonded to said polymeric material.

The aforementioned process with all its preferred features or any preferred embodiments thereof, or any combination of features or combination of preferred embodiments thereof, disclosed herein, is referred herein as "the process of the invention".

The process of the invention provides for an efficient drying of moist polymeric materials and reduces or even eliminates agglomeration of the moist polymeric material during drying preferably combined with high purity (or equally lower amount of impurities) of the dried polymeric material and/or prolonged storage stability; the process of the invention preferably further combines lower energy demands.

Preferably, the process of the invention comprises the steps of:

filtering the moist polymeric material to remove an amount of volatiles and carbohydrates to obtain a pre-dried polymeric material having a volatiles content $VC_{pre\text{-}dried}$ (pre-drying step);

The process of the invention involving mixing the moist polymeric material with an aqueous solution of a carbohydrate may afford further advantages. For example, said process of the invention allows polymeric materials that may be intrinsically sensitive to drying at elevated temperatures e.g. temperatures higher than 30° C., to be dried in a fluidized bed at somewhat higher temperature without the polymeric material been decomposed or rendered sticky or agglomerated since the fluidized bed allows for shorter time at the higher temperature, which leads to improved quality of the dried polymeric material. Particularly for APIs, this represents an important step forward. Further, said process may also account for an enhanced throughput of the fluidized bed that on its own accord results in a fluidized bed demanding significantly less energy in order to remove volatiles e.g. water from a given mass of a moist polymeric material. Furthermore, the process of the invention may offer enhanced control over the volatiles content, most specifically in achieving a desired target volatiles content for the dried polymeric material; this is of extreme importance since the volatiles content of the dried polymeric material impacts its storage stability.

Preferably, the process of the invention comprises the steps of:
mixing the moist polymeric material with an aqueous solution of a carbohydrate to afford a mixture of the moist polymeric material with the carbohydrate; and
filtering the mixture of the moist polymeric material with the carbohydrate to remove an amount of volatiles to obtain a pre-dried polymeric material having a volatiles content $VC_{pre-dried}$ (pre-drying step);
fluidizing the pre-dried material in a fluidized bed in order to further remove an amount of volatiles to obtain the dried polymeric material having a volatiles content $VC_{dried}$ (fluidized bed drying step); and
withdrawing and collecting the dried polymeric material from the fluidized bed; wherein $VC_{pre-dried}$ is higher than $VC_{dried}$.

Preferably in the process of the invention the filtering is performed via any one of the techniques selected from the group consisting of centrifuge, belt filtering, pressure filtering, vacuum suction filtering and combinations thereof. More preferably, in the process of the invention the filtering is performed via any one of the techniques selected from the group consisting of centrifuge, pressure filtering and combinations thereof. When the filtration is performed via pressure filtration via for example a nutsch filter the preferred pressure applied may range from 1.1 to 7 bar. When the filtration is performed via vacuum suction then the suction may range from 1 to 900 mbar.

Preferably in the process of the invention the pre-drying step further comprises blowing or sucking a gas, through the moist polymeric material, more preferably said gas is an inert gas, most preferably nitrogen. The further advantage achieved by blowing or sucking a gas through a moist polymeric material allows enhanced control over achieving a desired $VC_{pre-dried}$ at the pre-drying step of the process of the invention and/or may drive off flourine non-permanently bonded to the polymeric material. For example this can be done by taking measurements of the $VC_{pre-dried}$ over time and during the pre-drying step of the process and once the $VC_{pre-dried}$ is reached to stop the blowing or sucking the gas.

Preferably in the process of the invention no heating is applied in the pre-drying step. This has the advantageous effect of reducing even further the energy demands of the process of the invention without compromising any one of the rest of the advantages of the process of the invention.

Unless the context clearly indicates otherwise, as used herein singular forms of the terms herein (for example polymer, composition) are to be construed as including the plural form and vice versa.

For all upper and lower boundaries of any parameters given herein, the boundary value is included in each range for each parameter. All combinations of minimum and maximum values of the parameters described herein may be used to define the parameter ranges for various embodiments and preferences of the invention.

In the context of the present invention unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying in between the more preferred and the less preferred of said alternatives, is itself preferred to said less preferred value and also to each value lying between said less preferred value and said intermediate value.

By "pre-drying step" of the process of the invention and all the relevant preferred features or embodiments associated to said "pre-drying step" is meant herein the process step of the invention wherein heating and/or filtering of the mixture of the moist polymeric material to remove an amount of volatiles to obtain a pre-dried polymeric material having a volatiles content $VC_{pre-dried}$ takes place.

By "fluidized bed drying step" of the process of the invention and all the relevant preferred features or embodiments associated to said "fluidized bed drying step" is meant herein the process step of the invention wherein fluidizing of the pre-dried material in a fluidized bed in order to further remove an amount of volatiles to obtain the dried polymeric material having a volatiles content $VC_{dried}$ takes place.

By "fluidized bed" is herein meant a solid particulate substance converted from a static solid-like state to a dynamic fluid-like state when a fluid (liquid or gas) is passed up through the solid particulate substance. Fluidized beds are for example described in http://en.wikipedia.org/wiki/Fluidized_bed, 8 Aug. 2013.

By "polymeric material" is meant herein, a polymer or a composition containing a polymer and at least another distinct chemical substance. The polymeric material may be produced by any known polymerization method for example via polycondensation, free-radical polymerization, atom transfer radical polymerization; in the absence or presence of solvents the latter being typically organic solvents or water e.g. emulsion polymerization, suspension polymerization; in case the polymeric material is a composition containing a polymer and at least another distinct chemical substance, mixing of the polymer with the at least another distinct chemical substance may be also involved and it can be accomplished by any known method of mixing substances for example compounding, high-shear mixing, low-shear mixing, magnetic mixing, ultrasonic mixing. The polymeric material may be an at least partially crosslinked or non-crosslinked polymeric material. Examples of polymeric materials include but are not limited to a polymer or copolymer from α,β-unsaturated acid, salts, esters or amide derivatives thereof; or a polyamide; or a polyesterimide; or a polyester; or a polyolefine; or a polyurethane; or a polyamine; or combinations thereof.

By "volatiles" is meant herein substances e.g. water, organic solvents, organic substances, that are driven off from a sample e.g. a polymeric material that contains said volatiles upon heating said sample at 160° C. for 45 min in a halogen moisture analyser. In the context of the present invention the volatiles are typically mainly water, preferably the water content of the volatiles is higher than 90% w/w on total volatiles, more preferably higher than 95% w/w on total volatiles, most preferably higher than 98% w/w on total volatiles, especially higher than 99% w/w on total volatiles.

By "volatiles content" abbreviated as "VC" is meant herein the amount of volatiles contained in sample of material e.g. polymeric material.

By "moist polymeric material" is meant herein a mixture comprising a polymeric material and volatiles and having a $VC_{moist}$.

By "pre-dried polymeric material" is meant herein a polymeric material derived upon the pre-drying step of the process of the invention and having a $VC_{pre-dried}$. The pre-dried polymeric material is a mixture of a polymeric material and volatiles and its $VC_{pre-dried}$ is as disclosed herein.

By "dried polymeric material" is meant herein a polymeric material derived upon the fluidized bed drying step of the process of the invention and having a $VC_{dried}$. The dried polymeric material is either a polymeric material or a mixture of a polymeric material and volatiles depending on its $VC_{dried}$ as the latter is disclosed herein.

By "volatiles content of the moist polymeric material" abbreviated as "$VC_{moist}$" is meant herein the amount of volatiles contained in a sample of a pre-dried polymeric material; said $VC_{moist}$ is calculated according to the following formula:

$$VC_{moist}(\%) = 100 \times (M_{moist} - M_{moist\ upon\ heating\ at\ 160°\ C.\ for\ 45\ min}) / M_{moist} \quad (1)$$

$VC_{moist}$ is herein measured with a halogen moisture analyser wherein a light metal scale pan is tarred on the integrated analytical balance of the halogen moisture analyser before weighing the mass of a moist polymeric material; afterwards 2 g of a moist polymeric material ($M_{moist}$) are scattered over the whole scale pan surface and said sample is heated at 160° C. for 45 min; upon said heating, the $M_{moist\ upon\ heating\ at\ 160°\ C.\ for\ 45\ min}$ in the analytical balance is recorded.

By "volatiles content of the pre-dried polymeric material" abbreviated as "$VC_{pre-dried}$" is meant herein the amount of volatiles contained in a sample of a pre-dried polymeric material; said $VC_{pre-dried}$ is calculated according to the following formula:

$$VC_{pre-dried}(\%) = 100 \times (M_{pre-dried} - M_{pre-dried\ upon\ heating\ at\ 160°\ C.\ for\ 45\ min}) / M_{pre-dried} \quad (2)$$

$VC_{pre-dried}$ is herein measured with a halogen moisture analyser wherein a light metal scale pan is tarred on the integrated analytical balance of the halogen moisture analyser before weighing the mass of a pre-dried polymeric material; afterwards 2 g of a moist polymeric material ($M_{pre-dried}$) are scattered over the whole scale pan surface and said sample is heated at 160° C. for 45 min; upon said heating, the $M_{pre-dried\ upon\ heating\ at\ 160°\ C.\ for\ 45\ min}$ in the analytical balance is recorded.

By "volatiles content of the dried polymeric material" abbreviated as "$VC_{dried}$" is meant herein the amount of volatiles contained in a sample of a dried polymeric material; said $VC_{dried}$ is calculated according to the following formula:

$$VC_{dried}(\%) = 100 \times (M_{dried} - M_{dried\ upon\ heating\ at\ 160°\ C.\ for\ 45\ min}) / M_{dried} \quad (3)$$

$VC_{dried}$ is herein measured with a halogen moisture analyser wherein a light metal scale pan is tarred on the integrated analytical balance of the halogen moisture analyser before weighing the mass of a moist polymeric material; afterwards 2 g of a moist polymeric material ($M_{dried}$) are scattered over the whole scale pan surface and said sample is heated at 160° C. for 45 min; upon said heating, the $M_{dried\ upon\ heating\ at\ 160°\ C.\ for\ 45\ min}$ in the analytical balance is recorded.

In formulae 1, 2 and 3:
- by "M" is meant "Mass";
- by "$M_{moist}$" is meant mass of the moist polymeric material;
- by "$M_{pre-dried}$" is meant mass of the pre-dried polymeric material;
- by "$M_{dried}$" is meant mass of the dried polymeric material;
- by "$M_{moist\ upon\ heating\ at\ 160°\ C.\ for\ 45\ min}$" is meant mass of the moist polymeric material upon heating at 160° C. for 45 min;
- by "$M_{pre-dried\ upon\ heating\ at\ 160°\ C.\ for\ 45\ min}$" is meant mass of the pre-dried polymeric material upon heating at 160° C. for 45 min;
- by "$M_{dried\ upon\ heating\ at\ 160°\ C.\ for\ 45\ min}$" is meant mass of the dried polymeric material upon heating at 160° C. for 45 min.

In the context of the present invention the relationship between $VC_{moist}$, $VC_{pre-dried}$ and $VC_{dried}$ is as follows: $VC_{moist}$ is higher than $VC_{pre-dried}$ and $VC_{pre-dried}$ is higher than $VC_{dried}$ ($VC_{moist} > VC_{pre-dried} > VC_{dried}$).

Preferably in the process of the invention the $VC_{pre-dried}$ is at least 5%, more preferably at least 8%, most preferably at least 10%, especially at least 15%, more especially at least 20%, most especially at least 20%, for example at least 25%, for example at least 30%. Preferably in the process of the invention the $VC_{pre-dried}$ is at most 90%, more preferably at most 80%, most preferably at most 70%, especially at most 65%, more especially at most 60%, most especially at most 55%, for example at most 50%, for example at most 45%, for example at most 42%. Preferably in the process of the invention the $VC_{pre-dried}$ is at most 42%.

Preferably in the process of the invention the $VC_{dried}$ is at least 0%, more preferably at least 1%, most preferably at least 3%, especially at least 6%, more especially at least 8%, most especially at least 10%, for example at least 12%, for example at least 14%. Preferably in the process of the invention the $VC_{dried}$ is at most 50%, more preferably at most 40%, most preferably at most 35%, especially at most 30%, more especially at most 28%, most especially at most 25%, for example at most 22%, for example at most 20%, for example at most 18%.

In a preferred embodiment, the volatile content of the polymeric material is changed during the process according to the invention so that 99% $VC_{moist} > VC_{pre-dried} > 75\%$ $VC_{moist}$, more preferably 98% $VC_{moist} > VC_{pre-dried} > 90\%$ $VC_{moist}$ or 90% $VC_{moist} > VC_{pre-dried} > 80\%$ $VC_{moist}$.

For the second step of the drying it is preferred that the volatile content of the polymeric material is changed during the process according to the invention so that: 90% $VC_{pre-dried} > VC_{dried} > 10\%$ $VC_{pre-dried}$, more preferably 80% $VC_{pre-dried} > VC_{dried} > 20\%$ $VC_{pre-dried}$.

Overall for the first step and the second step of the process according to the invention, it is preferred that the volatile content of the polymeric material is changed so that 80% $VC_{moist} > VC_{dried} > 8\%$ $VC_{moist}$, more preferably 70% $VC_{moist} > VC_{dried} > 10\%$ VC moist.

The progress of drying in either the pre-drying or the fluidized bed drying step of the process of the invention may be monitored by measuring the $VC_{pre-dried}$ or $VC_{dried}$, respectively. In the case of the monitoring of the progress of the drying of the fluidized bed drying step of the process of the invention, this can also be done by measuring the difference in the moisture content on entry to the fluidized bed and on exit from the fluidized bed, of the gas used to fluidize the pre-dried material.

The pre-dried polymeric material is further dried in a fluidized bed that may operate in either a batch or continuous mode. Preferably, the fluidized bed operates in a continuous mode since this allows for enhanced consistency in the purity of the dried polymeric material. In the continuous mode the pre-dried polymeric material is charged with a rate of 50-200 kg/h into the fluidized bed and the fluidized bed may contain 100-500 kg of dried polymeric material of the same kind of the pre-dried polymeric material obtained for example from previous batches. In either a batch or continuous mode of operation of the fluidized bed the pre-dried polymeric material is fluidized with a stream of gas, preferably the gas is an inert gas, more preferably the gas is nitrogen, said gas being at a temperature that may range from 20 to 60° C., and having a velocity of 0.02-3.5 m/s. The temperature of the product inside the fluidized bed may be maximum the temperature of the gas, preferably the temperature of the product inside the fluidized bed is at most 50° C., most preferably is at most 40° C. The progress of this step of the process of the invention may be monitored, either by drawing a sample and analyzing its VC with a moisture analyser or by comparing the temperature and/or the moisture of the gas going into the fluidized bed with the temperature and/or the moisture of the gas exiting the fluidized bed.

In the batch mode of operation of the fluidized bed the drying is stopped after the desired $VC_{dried}$ is reached. In the continuous mode 30-150 kg/h of dried polymeric material is removed from the fluidized bed once sufficient drying has been achieved. Sufficient drying may be determined either when a measurement of the $VC_{dried}$ indicates that the desired $VC_{dried}$ has been reached or by comparing the temperature and/or the moisture of the gas going into the fluidized bed with the temperature and/or the moisture of the gas exiting the fluidized bed.

In the process of the invention the moist polymeric material comprises at least a polymeric material, said polymeric material comprises fluorine permanently bonded to said polymeric material. Preferably the amount of the permanently bound fluorine to the polymeric material is in the range of 7-14% w/w, more preferably in the range of 9-11% w/w on the weight of the polymeric material.

Preferably in the process of the invention the moist polymeric material comprises a polymer or copolymer from $\alpha,\beta$-unsaturated acid, salts, esters or amide derivatives thereof; a polyamide; a polyesterimide; a polyester; a polyolefine; a polyurethane; a polyamine; a polyepoxy; a polyether; and polymeric material comprises fluorine permanently bonded to said polymeric material. More preferably, in the process of the invention the moist polymeric material comprises a moist polymer or copolymer as those disclosed in WO 2011/119422 A1, WO 10022382 A2, WO 2005/097081 A1, WO 2010/022381 A1, WO 2010/022382 A2, WO 2010/022383 A2 and all of them are herein incorporated by reference in their entirety. More preferably, in the process of the invention the moist polymeric material comprises a moist polymer or copolymer from $\alpha,\beta$-unsaturated acid, salts, esters or amide derivatives thereof. Most preferably, in the process of the invention the moist polymeric material comprises a polymer or copolymer from acrylic and/or methacrylic acid, salts, esters or amide derivatives thereof. Especially, in the process of the invention the moist polymeric material comprises a polymer or copolymer as those disclosed in WO 2011/119422 A1, WO 10022382 A2, WO 2005/097081 A1, WO 2010/022381 A1, WO 2010/022382 A2, WO 2010/022383 A2, U.S. Pat. No. 4,426,507 and all of them are herein incorporated by reference in their entirety. The polymeric material may be negatively charged (anionic polymeric material) or positively charged (cationic polymeric material) or bearing no charge. The polymeric material may be in the form of a powder, or in the form of a gel, or in the form of particles. In case the polymeric material is in the form of particles these particles may come in various shapes, e.g. spheres, ellipses, cones, cylinders, rod or rod-like, rice-like, octahedral, cubic, tabular or irregular, etc.

Especially, in the process of the invention the moist polymeric material comprises an at least partially crosslinked or non-crosslinked polymeric material. More especially, in the process of the invention, the moist polymeric material comprises an at least partially crosslinked polymeric material. Examples of an at least partially crosslinked polymeric material include but are not limited to at least partially crosslinked polymer or copolymer from $\alpha,\beta$-unsaturated acid, salts, esters or amide derivatives thereof; or at least partially crosslinked polyamide; or at least partially crosslinked polyesterimide; or at least partially crosslinked polyester; or at least partially crosslinked polyolefine; or at least partially crosslinked polyurethane; or at least partially crosslinked polyamine; or at least partially crosslinked polyepoxy; or at least partially crosslinked polyether.

Preferably in the process of the invention the moist polymeric material comprises an at least partially crosslinked polymeric material comprising:
 i) a substituted acrylic acid derivative such as ester, amide or salt, in 50-96% w/w on polymeric material; preferably said acrylic acid derivative such as ester, amide or salt is calcium 2-fluoroacrylate in 85-95% w/w on polymeric material; and
 ii) one or more alkenes in 1-50% w/w on polymeric material; preferably said alkene is octadiene in 3-7% w/w on polymeric material; and
 iii) divinylbenzene in 3-7% w/w on polymeric material.

The aforementioned preferred embodiment of the process of the invention enables efficient drying of this type of moist polymeric materials in a large scale and without agglomeration.

Preferably in the process of the invention the carbohydrate is a mono- and/or poly-saccharide. More preferably in the process of the invention the carbohydrate is sorbitol or glucose or other carbohydrates like for example fructose and galactose, and disaccharide including for example maltose and lactose. Most preferably, the carbohydrate is sorbitol.

Preferably in the process of the invention the concentration of the carbohydrate in said carbohydrate's aqueous solution is at least 1% w/w, more preferably is at least 2% w/w, most preferably is at least 3% w/w, especially is at least 4% w/w, more especially is at least 5% w/w, for example is at least 10% w/w, for example is at least 15% w/w, for example is at least 20% w/w on total weight of said carbohydrate's aqueous solution. Preferably in the process of the invention the concentration of the carbohydrate in said carbohydrate's aqueous solution is at most 95% w/w, more preferably is at most 90% w/w, most preferably is at most 80% w/w, especially is at most 75% w/w, more especially is at most 70% w/w, for example is at most 65% w/w, for example is at most 60% w/w, for example is at most 55% w/w, for example is at most 50% w/w, for example is at most 45% w/w, for example is at most 40% w/w, on total weight of said carbohydrate's aqueous solution. Preferably in the process of the invention the concentration of the carbohydrate in said carbohydrate's aqueous solution is at least 5% and at most 60% w/w on total weight of said carbohydrate's aqueous solution. Preferably in the process of the invention the concentration of the carbohydrate in said carbohydrate's aqueous solution is at least 25 and at most 45% w/w on total weight of said carbohydrate's aqueous solution. Preferably, in the process of the invention the concentration of the carbohydrate in said carbohydrate's aqueous solution is at least 25 and at most 35% w/w on total weight of said carbohydrate's aqueous solution. Preferably, in the process of the invention the concentration of the carbohydrate in said carbohydrate's aqueous solution is about 30% w/w on total weight of said carbohydrate's aqueous solution.

In another aspect the invention relates also to a dried polymeric material obtainable by the process of the invention wherein the moist polymeric material is a moist at least partially crosslinked polymeric material comprising:
  i) a substituted acrylic acid derivative such as ester, amide or salt, in 50-96% w/w on polymeric material; preferably said acrylic acid derivative such as ester, amide or salt is calcium 2-fluoroacrylate in 85-95% w/w on polymeric material; and
  ii) one or more alkenes in 1-50% w/w on polymeric material; preferably said alkene is octadiene in 3-7% w/w on polymeric material; and
  iii) divinylbenzene in 3-7% w/w on polymeric material; and
wherein said dried polymeric material contains fluorine non-permanently bonded to the polymeric material, herein mentioned as fluorine impurities, of at most 20 ppm, preferably lower than 20 ppm on dried polymeric material. Due to surprisingly low level of fluorine impurities, the aforementioned dried polymeric material has reduced toxicity and improved storage stability.

In another aspect the invention provides for a use of a process of the invention for producing dried polymeric materials from drying moist polymeric materials such as those described herein.

In another aspect the invention provides for a use of a process of the invention for drying a moist polymeric material, wherein the polymeric material is an active pharmaceutical ingredient (API).

In another aspect the invention provides for a use of a dried polymeric material as this is disclosed herein obtainable by the process of the invention.

In another aspect the invention provides for a use of a dried polymeric material as this is disclosed herein obtainable by the process of the invention, in pharmaceutical applications.

In another aspect the invention provides for a use of a dried polymeric material as this is disclosed herein obtainable by the process of the invention wherein said dried polymeric material contains impurities of at most 500 ppm, preferably of at most 200 ppm, more preferably of at most 100 ppm, on dried polymeric material.

In another aspect the invention provides for a use of a dried polymeric material as this is disclosed herein obtainable by the process of the invention wherein said dried polymeric material contains impurities of at most 500 ppm preferably of at most 200 ppm, more preferably of at most 100 ppm, on dried polymeric material, in pharmaceutical applications.

In another aspect the invention provides for a use of a dried polymeric material in a pharmaceutical composition, said dried polymeric material is obtainable by the process of the invention wherein the moist polymeric material comprises an at least partially crosslinked polymeric material comprising:
  i) a substituted acrylic acid derivative such as ester, amide or salt, in 50-96% w/w on polymeric material; preferably said acrylic acid derivative such as ester, amide or salt is calcium 2-fluoroacrylate in 85-95% w/w on polymeric material; and
  ii) one or more alkenes in 1-50% w/w on polymeric material; preferably said alkene is octadiene in 3-7% w/w on polymeric material; and
  iii) divinylbenzene in 3-7% w/w on polymeric material; and
wherein said dried polymeric material contains fluorine non-permanently bonded to the polymeric material, herein mentioned as fluorine impurities, of at most 20 ppm, preferably lower 20 ppm on dried polymeric material.

In another aspect the invention provides for a use of a dried polymeric material obtainable by the process of the invention in the preparation of suspensions; in the production of adhesives; in the production of ion exchange resins; as thickeners in the production of paints and varnishes; as sizing agents for natural and synthetic fibres in textiles; as flocculation agents in the pulp-and-paper, coal extraction, mining industries; in primers for leather tanning; as anti-frosting liquids in aviation; as protective agents in the drilling technology; as structurization agents for soils and grounds in; as coagulation agents in the treatment of waste waters, fine dispersions and latexes.

In another aspect the invention provides for a use of a dried polymeric material obtainable by the process of the invention in automotive, marine, aerospace, medical, defense, sports/recreational, architectural, bottling, household and machinery applications.

Examples of automotive applications include but are not limited to car parts, agricultural machines, composite structures, ceramic structures.

Examples of marine applications include but are not limited to ship parts, boats parts, boats.

Examples of aerospace applications include but are not limited to planes, helicopters, composite structures, ceramic structures.

Examples of medical applications include but are not limited to artificial joints, meshes, woven or non-woven sheets, tapes, ribbons, bands, cables, tube-like products for e.g. ligament replacement, composite structures, ceramic structures.

Examples of defence applications include but are not limited to ballistic protection, body armour, ballistic vests, ballistic helmets, ballistic vehicle protection, composite structures, ceramic structures.

Examples of sports/recreational applications include but are not limited to fencing, skates, skateboarding, snowboarding, suspension lines on sport parachutes, paragliders, kites, kite lines for kite sports, climbing equipment, composite structures, ceramic structures.

Examples of architectural applications include but are not limited to windows, doors, (pseudo-)walls, cables.

Examples of household applications include but are not limited to household appliances, white goods, furniture, office furniture, domestic appliances, computer housings.

Examples of machinery applications include but are not limited to can and bottle handling machine parts, moving parts on weaving machines, bearings, gears, composite structures, ceramic structures.

Yet, another aspect of the invention is a process according to the Examples 1-6.

Yet, another aspect of the invention is a product obtainable by the process according to the Examples 1-6.

Many other variations embodiments of the invention will be apparent to those skilled in the art and such variations are contemplated within the broad scope of the present invention.

All embodiments disclosed herein may be combined with each other and/or with preferred elements e.g. features, ranges, of the present invention.

Further aspects of the invention and preferred features thereof are given in the claims herein.

The invention will now be described in detail with reference to the following non limiting examples which are by way of illustration only.

EXAMPLES

Examples 1-6 are examples according to the invention (inventive examples), whilst Comparative Examples 1 and 2 are non-inventive examples and Background Examples 7 and 8 are outside the claimed scope.

The moist polymeric material used in the Examples 1-4, 6 and Comparative Examples 1 and 2, was an aqueous suspension (water was the main volatile) of an at least partially crosslinked polymer comprising:
 i) calcium 2-fluoroacrylate in 90% w/w on polymeric material; and
 ii) octadiene in 5% w/w on polymeric material; and
 iii) divinylbenzene in 5% w/w on polymeric material;
wherein the amount of the crosslinked polymer was 50% w/w on aqueous suspension (=moist polymeric material).

The moist polymeric material used in Example 5 was an aqueous suspension (water was the main volatile) of an at least partially crosslinked polymer comprising:
 i) calcium 2-fluoroacrylate in 90% w/w on polymeric material; and
 ii) divinylbenzene in 10% w/w on polymeric material;
wherein the amount of the crosslinked polymer was 50% w/w on aqueous suspension (=moist polymeric material).

The moist polymeric material used in Background Example 7 was an aqueous suspension (water was the main volatile) of an at least partially crosslinked polymer comprising:
 i) calcium acrylate in 90% w/w on polymeric material; and
 ii) octadiene in 5% w/w on polymeric material; and
 iii) divinylbenzene in 5% w/w on polymeric material;
wherein the amount of the crosslinked polymer was 50% w/w on aqueous suspension (=moist polymeric material).

The moist polymeric material used in Background Example 8 was an aqueous suspension (water was the main volatile) of an at least partially crosslinked polymer (polyamine) comprising:
 i) alkylpolyamine in 70% w/w on polymeric material; and
 ii) 1,3-dichlor-2-propanol in 30% w/w on polymeric material;
wherein the amount of the crosslinked polymer was 50% w/w on aqueous suspension (=moist polymeric material).

The aforementioned moist polymeric materials used in the Examples 1-8 and Comparative Examples 1 and 2, will be referred in the corresponding Examples as "the moist polymeric material".

Comparative Example 1

0.90 kg of the moist polymeric material was mixed with 0.70 kg of an aqueous solution of sorbitol wherein the concentration of sorbitol in its aqueous solution was 30% w/w on total weight of sorbitol's aqueous solution. The VC of the mixture of the moist polymeric material with the aqueous solution of sorbitol was 60%.

Fluidized bed drying step: Subsequently, the mixture of the moist polymeric material with the aqueous solution of sorbitol was introduced into a small fluidized bed of the type DMR Mini; when attempting to fluidize the material with a stream of air, agglomerates were formed which were not readily broken up during drying and led to hard lumps in the dried polymeric material collected. 0.65 kg of agglomerated dried polymeric material with a $VC_{dried}$ of 14% were collected. The fluorine impurities in the dried polymeric material were equal to 25 ppm on total weight of the dried polymeric material. The drying of the moist polymeric material has taken about 3 h.

Comparative Example 2

0.32 kg of the moist polymeric material was mixed with 0.26 kg of an aqueous solution of sorbitol wherein the concentration of sorbitol in its aqueous solution was 30% w/w on total weight of sorbitol's aqueous solution.

Drying step: Subsequently, the mixture of the moist polymeric material with the aqueous solution of sorbitol was filtered with vacuum suction via a jacketed pressure filter at 30° C. for 2 min. Afterwards, the supernatant was removed, a vacuum of max. 25 mbar and a temperature of 30-34° C. were maintained for 32 h. Some agglomeration (~10% w/w of the total weight of the dried polymeric material) was observed in the dried polymeric material. 0.25 kg of partly agglomerated dried polymeric material with a $VC_{dried}$ of 16.7% were collected. The fluorine impurities in the dried polymeric material were equal to 27 ppm on total weight of the dried polymeric material. The drying of the moist polymeric material has taken about 32 h.

Example 1

2.8 kg of the moist polymeric material was mixed with 2.2 kg of an aqueous solution of sorbitol wherein the concentration of sorbitol in its aqueous solution was 30% w/w on total weight of sorbitol's aqueous solution.

Pre-drying step: Subsequently, the mixture of the moist polymeric material with the aqueous solution of sorbitol was filtered portionwise with a centrifuge of the type BHG 8212/0830713 for 5 min at 23° C. and at $10^4$ rotations/min. 3.27 kg of free-flowing pre-dried polymeric material with a $VC_{pre-dried}$ of 41.3% were collected.

Fluidized bed drying step: The pre-dried material thus prepared was introduced into a small fluidized bed of the type DMR WFP-8 and it was fluidized with a stream of pre-heated air the temperature of which was maintained throughout the entire duration of this process step at 60° C. with 120-132 m³/h at 82-100% ventilator velocity. The temperature at which the pre-dried polymeric material was exposed during this process step ranged from 33° C. to 45° C.; the temperature of the air leaving the fluidized bed increased during the duration of this process step from 40° C. to 52° C. After 1 h of continuous operation of the fluidized bed, 2.05 kg of free-flowing dried polymeric material with a $VC_{dried}$ of 15.9% were collected. No visible signs of agglomeration were observed in the dried polymeric material. The fluorine impurities in the dried polymeric material were lower than 20 ppm on total weight of the dried polymeric material. Pre-drying and fluidized bed drying were completed in less than 3 h.

Example 2

0.35 kg of the moist polymeric material was mixed with 0.28 kg of an aqueous solution of sorbitol wherein the concentration of sorbitol in its aqueous solution was 30% w/w on total weight of sorbitol's aqueous solution.

The drying process applied in Example 2 was differed from that of Example 1 in that the pre-drying step was different. More particularly, the process applied in Example 2 was as follows:

Pre-drying step: Subsequently, the mixture of the moist polymeric material with the aqueous solution of sorbitol was filtered using nitrogen pressure of 1.8 bar via a jacketed pressure filter at 30° C. for 2 min. Afterwards, the supernatant was removed, the nitrogen pressure was maintained by blowing nitrogen through the pressure filter for 3 h at 30-34° C. 0.4 kg of free-flowing pre-dried polymeric material with a $VC_{pre-dried}$ of 42.3% were collected.

Fluidized bed drying step: Same as in Example 1. 0.23 kg of free-flowing dried polymeric material with a $VC_{dried}$ of 15.7% was collected. No visible signs of agglomeration were observed in the dried polymeric material. The fluorine impurities in the dried polymeric material were lower than 20 ppm on total weight of the dried polymeric material. Pre-drying and fluidized bed drying were completed in less than 6 h.

Example 3

14 kg of the moist polymeric material was mixed with 11 kg of an aqueous solution of sorbitol wherein the concentration of sorbitol in its aqueous solution was 30% w/w on total weight of sorbitol's aqueous solution.

The drying process applied in Example 3 was differed from that of Example 1 in that the pre-drying step was different. More particularly, the process applied in Example 3 was as follows:

Pre-drying step: Subsequently, the mixture of the moist polymeric material with the aqueous solution of sorbitol was filtered using vacuum suction via a belt filter from BHS at 30° C. In the first zone the mother liquor is removed via vacuum suction, in the subsequent zones pre-heated nitrogen (~35° C.) is blown through the filter cake to achieve a pre-drying effect. 16.6 kg of free-flowing pre-dried polymeric material with a $VC_{pre-dried}$ of 41.8% was collected.

Fluidized bed drying step: Same as in Example 1. 11 kg of free-flowing dried polymeric material with a $VC_{dried}$ of 15.6% were collected. No visible signs of agglomeration are observed in the dried polymeric material. The fluorine impurities in the dried polymeric material were lower than 20 ppm on total weight of the dried polymeric material. Pre-drying and fluidized bed drying were completed in less than 12 h.

Example 4

840 kg of the moist polymeric material was mixed with 660 kg of an aqueous solution of sorbitol wherein the concentration of sorbitol in its aqueous solution is 30% w/w on total weight of sorbitol's aqueous solution.

The drying process applied in Example 4 was differed from that of Example 1 in that the fluidized bed drying step was different. More particularly, the process applied in Example 4 was as follows:

Pre-drying step: same as in Example 1. 1050 kg of free-flowing pre-dried polymeric material with a $VC_{pre-dried}$ of 42.1% were collected.

Fluidized bed drying step: 300 kg dried polymeric material from a previous batch were charged into the fluidized bed and said amount of dried polymeric material from a previous batch were fluidized with a stream of pre-heated nitrogen (40° C.) at a velocity of 2.5 m/s. Then 150 kg/h of the pre-dried material ($VC_{pre-dried}$ of 42.1%) collected from the pre-drying step were introduced into the fluidized bed. After 6 h, dried polymeric material was removed at a pace of 105 kg/h. The $VC_{dried}$ was 14.6%. No visible signs of agglomeration were observed in the dried polymeric material. The fluorine impurities in the dried polymeric material were lower than 20 ppm on total weight of the dried polymeric material. Pre-drying and fluidized bed drying were completed in less than 24 h.

Example 5

1.3 kg of the moist polymeric material was mixed with 1 kg of an aqueous solution of sorbitol wherein the concentration of sorbitol in its aqueous solution is 30% w/w on total weight of sorbitol's aqueous solution Pre-drying step: Subsequently, the mixture of the moist polymeric material with the aqueous solution of sorbitol was filtered portionwise with a centrifuge of the type BHG 8212/0830713 for 5 min at 23° C. and at $10^4$ rotations/min. Free-flowing pre-dried polymeric material with a $VC_{pre-dried}$ of 40.9% was collected.

Fluidized bed drying step: same as in Example 1. 1 kg of free-flowing dried polymeric material with a $VC_{dried}$ of 15.5% were collected. No visible signs of agglomeration were observed in the dried polymeric material. The fluorine impurities in the dried polymeric material were lower than 20 ppm on total weight of the dried polymeric material. Pre-drying and fluidized bed drying were completed in less than 4 h.

Example 6

2.0 kg of the moist polymeric material was mixed with 1.5 kg of an aqueous solution of glucose wherein the concentration of glucose in its aqueous solution is 30% w/w on total weight of glucose's aqueous solution.

Pre-drying step: Subsequently, the mixture of the moist polymeric material with the aqueous solution of glucose was filtered portionwise with a centrifuge of the type BHG 8212/0830713 for 5 min at 23° C. and at $10^4$ rotations/min. 2.3 kg of free-flowing pre-dried polymeric material with a $VC_{pre-dried}$ of 41.8% was collected.

Fluidized bed drying step: same as in Example 1. 1.5 kg of free-flowing dried polymeric material with a $VC_{dried}$ of 15.9% were collected. No visible signs of agglomeration were observed in the dried polymeric material. The fluorine impurities in the dried polymeric material were lower than 20 ppm on total weight of the dried polymeric material. Pre-drying and fluidized bed drying were completed in less than 5 h.

Background Example 7

1.0 kg of the moist polymeric material was mixed with 0.7 kg of an aqueous solution of sorbitol wherein the concentration of sorbitol in its aqueous solution is 30% w/w on total weight of sorbitol's aqueous solution Pre-drying step: Subsequently, the mixture of the moist polymeric material with the aqueous solution of sorbitol was filtered portionwise with a centrifuge of the type BHG 8212/0830713 for 5 min at 23° C. and at $10^4$ rotations/min. 1.16 kg of free-flowing pre-dried polymeric material with a $VC_{pre-dried}$ of 41.3% were collected.

Fluidized bed drying step: same as in Example 1. 0.7 kg of free-flowing dried polymeric material with a $VC_{dried}$ of 15.4% were collected. No visible signs of agglomeration were observed in the dried polymeric material. Pre-drying and fluidized bed drying were completed in less than 5 h.

Background Example 8

Pre-drying step: 0.4 kg of the moist polymeric material were filtered using nitrogen pressure of 1.8 bar via a jacketed pressure filter at 23° C. for 2 min. 0.2 kg of free-flowing pre-dried polymeric material with a $VC_{pre-dried}$ of 70% were collected.

Fluidized bed drying step: same as in Example 1. 0.06 kg of free-flowing dried polymeric material with a $VC_{dried}$ of 15.0% were collected. No visible signs of agglomeration were observed in the dried polymeric material. Pre-drying and fluidized bed drying were completed in less than 4 h.

Upon comparing any one of the inventive Examples 1-6 with any one of Comparative Examples 1-2, it becomes evident that only the process of the invention provided an efficient drying of moist polymeric materials and eliminated agglomeration of the moist polymeric material during drying, combined with high purity (or equally lower amount of impurities) of the dried polymeric material and significantly lower energy demands for a given mass of a moist polymeric material and a given $VC_{dried}$ of a dried polymeric material.

Furthermore, upon comparing inventive Examples 1-4 and 6 with any one of Comparative Examples 1-2, it becomes evident that when the moist polymeric material comprises at least a partially crosslinked polymeric material comprising:
  i) a substituted acrylic acid derivative such as ester, amide or salt, in 50-96% w/w on polymeric material; preferably said acrylic acid derivative such as ester, amide or salt is calcium 2-fluoroacrylate in 85-95% w/w on polymeric material; and
  ii) one or more alkenes in 1-50% w/w on polymeric material; preferably said alkene is octadiene in 3-7% w/w on polymeric material; and
  iii) divinylbenzene in 3-7% w/w on polymeric material
then only the inventive process succeeds to dry said moist polymeric material without agglomeration of the dried polymeric material.

In addition, upon comparing any one of the inventive Examples 1-6 with any one of Comparative Examples 1-2, it becomes evident that the throughput of the fluidized bed used in the fluidized bed drying step of the inventive process was significantly enhanced without causing any agglomeration in the dried polymeric material.

Moreover, the inventive Examples 1-4 and 6 afforded dried polymeric materials with surprisingly lower fluorine impurities upon compared to the fluorine impurities of the dried polymeric materials of Comparative Examples 1-2. Due to the surprisingly low level of fluorine impurities, the dried polymeric materials of the inventive Examples 1-4 and 6 are expected to have reduced toxicity and improved storage stability.

The invention claimed is:

1. Process for drying a moist polymeric material comprising fluorine permanently bonded thereto to obtain a dried polymeric material having a reduced non-permanently bonded fluorine impurity level, comprising the steps of:
   (a) mixing the moist polymeric material with an aqueous solution of a carbohydrate to afford a mixture of the moist polymeric material with the carbohydrate;
   (b) heating and/or filtering the mixture of the moist polymeric material with the carbohydrate to remove an amount of volatiles to obtain a pre-dried polymeric material having a volatiles content $VC_{pre-dried}$ (pre-drying step);
   (c) fluidizing the pre-dried material in a fluidized bed in order to further remove an amount of volatiles to obtain the dried polymeric material having a volatiles content $VC_{dried}$ (fluidized bed drying step), the pre-dried material having a temperature of at most about 50° C. while in the fluidized bed; and
   (d) withdrawing and collecting the dried polymeric material from the fluidized bed;
wherein $VC_{pre-dried}$ is higher than $VC_{dried}$, and the moist polymeric material comprises at least a polymeric material, said polymeric material comprises fluorine permanently bonded to said polymeric material, wherein the $VC_{pre-dried}$ is at most 42% and wherein the dried polymeric material has a reduced non-permanently bonded fluorine level.

2. Process according to claim 1, wherein the pre-drying step of the process of claim 1, further comprises blowing or sucking a gas through the moist polymeric material.

3. The process of claim 2, wherein the gas is an inert gas.

4. The process of claim 3, wherein the inert gas is nitrogen.

5. Process according to claim 1 or 2, wherein the moist polymeric material comprises a polymer or copolymer selected from the group consisting of: α,β-unsaturated acid, salts, esters or amide derivatives thereof; a polyamide; a polyesterimide; a polyester; a polyolefine; a polyurethane; a polyamine; a polyepoxy; a polyether; or combinations thereof.

6. Process according to claim 1 or 2, wherein the moist polymeric material comprises an at least partially crosslinked polymeric material.

7. Process according to claim 6, wherein the at least partially crosslinked polymeric material comprises:
   i) a substituted acrylic acid derivative or an ester, amide or salt thereof, in the amount of 50-96% w/w of said polymeric material; and
   ii) one or more alkenes in the amount of 1-50% w/w of said polymeric material; and
   iii) divinylbenzene in the amount of 3-7% w/w of said polymeric material.

8. The process of claim 7, wherein said substituted acrylic acid derivative is calcium 2-fluoroacrylate in an amount of about 85-95% w/w of said polymeric material.

9. The process of claim 7, wherein said one or more alkenes is octadiene in an amount of about 3-7% w/w of said polymeric material.

10. The process according to claim 7, wherein said substituted acrylic acid derivative is calcium 2-fluoroacrylate in an amount of about 85 to about 95% w/w of said polymeric material.

11. The process according to claim 7, wherein said one or more alkenes is octadiene in an amount of about 3 to about 7% w/w of said polymeric material.

12. Process according to claim 1 or 2, wherein no heating is applied in the pre-drying step.

13. Process according to claim 1 or 2, wherein the $VC_{dried}$ is at least 10%.

14. The process of claim 13, wherein $VC_{dried}$ is measured with a halogen moisture analyser, wherein a light metal scale pan is tarred on a integrated analytical balance of the halogen moisture analyser before weighing the mass of a pre-dried polymeric material; afterwards 2 g of a moist polymeric material ($M_{dried}$) are scattered over the whole scale pan surface and said sample is heated at 160° C. for 45 min; upon said heating, the $M_{dried\ upon\ heating\ at\ 160°\ C.\ for\ 45\ min}$ in the analytical balance is recorded, and $VC_{dried}(\%) = 100 \times (M_{dried} - M_{dried\ upon\ heating\ at\ 160°\ C.\ for\ 45\ min})/M_{dried}$.

15. Process according to claim 1 or 2, wherein the carbohydrate is a mono- and/or poly-saccharide.

16. The process of claim 15, wherein the concentration of the aqueous solution of a carbohydrate is at least 5 and at most 60% w/w.

17. The process of claim 15, wherein the carbohydrate is sorbitol.

18. The process according to claim 15, wherein the concentration of the aqueous solution of a carbohydrate is at least 5 and at most 60% w/w.

19. The process according to claim 15, wherein the carbohydrate is sorbitol.

20. The process of claim 1, wherein $VC_{pre-dried}$ is measured with a halogen moisture analyser, wherein a light metal scale pan is tarred on a integrated analytical balance of the halogen moisture analyser before weighing the mass of a pre-dried polymeric material; afterwards 2 g of a moist polymeric material ($M_{pre-dried}$) are scattered over the whole scale pan surface and said sample is heated at 160° C. for 45 min; upon said heating, the $M_{pre-dried\ upon\ heating\ at\ 160°\ C.\ for\ 45\ min}$ in the analytical balance is recorded, and $VC_{pre-dried}(\%) = 100 \times (M_{pre-dried} - M_{pre-dried\ upon\ heating\ at\ 160°\ C.\ for\ 45\ min})/M_{pre-dried}$.

21. The process of claim 1 or claim 2, wherein $VC_{pre-dried}$ is at least 5%, at least 8%, at least 10%, at least 15%, at least 20%, at least 25%, or at least 30% by weight.

22. The process of claim 1 or claim 2, wherein $VC_{dried}$ is at least 0%, at least 1%, at least 3%, at least 6%, at least 8%, at least 10%, at least 12%, or at least 14% by weight.

23. The process of claim 1 or claim 2, wherein $VC_{dried}$ is at most 40%, at most 35%, at most 30%, at most 28%, at most 25%, at most 22%, or at most 20% by weight.

* * * * *

UNITED STATES PATENT AND TRADEMARK OFFICE
CERTIFICATE OF CORRECTION

PATENT NO. : 9,982,940 B2  
APPLICATION NO. : 14/420165  
DATED : May 29, 2018  
INVENTOR(S) : Hanbauer et al.

Page 1 of 1

It is certified that error appears in the above-identified patent and that said Letters Patent is hereby corrected as shown below:

On the Title Page

Please add the following text:  
Related U.S. Application Data  
(60) Provisional application No. 61/681,295, filed on August 9, 2012.

In the Specification

At Column 5/Line 30: "(1)" should read --formula (1)--

At Column 5/Line 30: "(2)" should read --formula (2)--

At Column 5/Line 64: "(3)" should read --formula (3)--

Signed and Sealed this
Twenty-seventh Day of August, 2019

Andrei Iancu
*Director of the United States Patent and Trademark Office*